United States Patent [19]
Heine

[11] Patent Number: 5,972,594
[45] Date of Patent: Oct. 26, 1999

[54] METHOD FOR SCREENING FOR REPRODUCTIVE TRACT INFLAMMATION AND PREECLAMPSIA USING NEUTROPHIL DEFENSINS

[75] Inventor: Robert Phillips Heine, Wexford, Pa.

[73] Assignee: University of Pittsburgh, Pittsburgh, Pa.

[21] Appl. No.: 08/796,666

[22] Filed: Feb. 5, 1997

[51] Int. Cl.⁶ .......................... G01N 33/53; G01N 33/48; C12Q 1/00; A61K 38/00

[52] U.S. Cl. ............................... 435/4; 435/7.1; 435/806; 436/63; 436/65; 436/811; 514/12

[58] Field of Search ................. 435/7.1, 4, 806; 436/63, 65, 811; 514/12

[56] References Cited

U.S. PATENT DOCUMENTS

| | | | |
|---|---|---|---|
| 4,705,777 | 11/1987 | Lehrer et al. | 514/12 |
| 5,126,257 | 6/1992 | Gabay et al. | 435/212 |
| 5,459,235 | 10/1995 | Selsted et al. | 530/300 |
| 5,556,782 | 9/1996 | Cooper et al. | 435/240.2 |

OTHER PUBLICATIONS

Rebelo et al., "Comparative Study of Lactoferrin and Other Blood Markers of Inflammatory Stress Between Preeclamptic and Normal Pregnancies," Eur. J. Obst. Gyne. 64: 167–173, Feb. 14, 1996.

Rein et al., "Use of a Lactoferrin Assay in the Differential Diagnosis of Female Genital Tract Infections and . . . " Sex. Trans. Dis. 23 (6): 517–521, Nov. Dec. 1996.

Panyutich et al., "An Enzyme Immunoassay for Human Defensins" J. of Immunol. Methods, 141: 149–155, 1991.

Panyutich et al., "Plasma Defensin Concentrations are Elevated in Patients with Septicemia or Bacterial Meningitis," J. Lab. Clin. Med. 122(2): 202–207, Aug. 1993.

Prieto et al., "Neutrophil Activation in Preeclampsia: Are Defensins and Lactoferrin Elevated in Preeclamptic Patients?" J. Rep. Med. 42 (1) 29–32, Jan. 1997.

Qu et al., "Susceptibility of *Neisseria gonorrhoeae* to Protegrins" Infect. Immun. 64 (4): 1240–1245, Aprl. 1996.

*Primary Examiner*—James C. Housel
*Assistant Examiner*—Gailene R. Gabel
*Attorney, Agent, or Firm*—Thorp Reed & Armstrong, LLP

[57] ABSTRACT

A method and apparatus for screening for reproductive tract inflammation and preeclampsia which utilizes the increase in neutrophil defensins to indicate that a patient is at risk of having reproductive tract inflammation or preeclampsia. The apparatus consists either an ELISA based measurement of defensins levels or a dipstick test that can be administered by the provider or self-administered by the patient.

10 Claims, 7 Drawing Sheets

METHOD FOR SCREENING FOR REPRODUCTIVE TRACT INFLAMMATION AND PREECLAMPSIA USING NEUTROPHIL DEFENSINS

BACKGROUND OF THE INVENTION

1. Field of the Invention

The present invention relates to a method and an apparatus for screening for reproductive tract inflammation and preeclampsia. More particularly, this invention concerns the method and apparatus for screening for reproductive tract inflammation and preeclampsia which utilize the presence of neutrophil defensins found in bodily fluids and tissues of a patient to indicate that the patient is at risk of having reproductive tract inflammation or preeclampsia.

2. Description of Related Art

Detection of reproductive tract inflammation and preeclampsia may be divided into two categories: diagnosis and screening. Diagnosis is a method of establishing the presence of a particular disease in a patient. Limitations of the current diagnostic methods include the high cost of a medical professional performing an invasive examination to take samples, run tests and analyze results as well as the inefficient utilization of the sensitive, yet expensive, diagnostic tests. For example, when polymerase chain reaction testing and ligase chain reaction testing, two standard diagnostic tests for sexually transmitted diseases, are performed, the medical professional must administer the test which results in an average of ten patients testing negative for every one patient that tests positive.

Optimally, a diagnostic test is employed only after a screening test indicates that the patient is at risk of having a disease in order to eliminate the unnecessary cost of expensive diagnostic tests. Screening is a method of establishing the absence of a particular disease or class of diseases in a patient. When a screening test indicates that a patient does not have a disease, in many cases the need for further diagnostic testing is eliminated. Such screening saves money for patients, health insurance companies and government health programs. In addition, screening provides a way for patients to avoid the discomfort associated with more invasive diagnostic procedures. The following are some of the conventional screening and diagnostic methods used to detect female reproductive tract inflammation and preeclampsia wherein the female reproductive tract inflammation include, but are not limited to, intraamniotic infection, pelvic inflammatory diseases and sexually transmitted diseases such as gonorrhea, chlamydia and trichomoniasis.

Pelvic inflammatory diseases may be caused by anaerobic bacterial infection, allergic reactions or prior infection by a sexually transmitted disease. In general the majority of pelvic inflammatory diseases are not symptomatic and therefore, go undetected. If undetected and untreated, pelvic inflammatory diseases may result in tubal factor infertility. Screening for upper reproductive tract inflammation such as salpingitis, cervicitis, endometritis and oophoritis generally includes a pelvic exam conducted by a physician. If manipulation of the cervix and palpitation of the adnexa produces severe pain during the pelvic exam, the patient is considered to be at risk for pelvic inflammatory disease. A diagnosis of pelvic inflammatory disease may be obtained by performing an endometrial biopsy or operative laparoscopy both of which are highly invasive and uncomfortable procedures conducted by a physician.

Intraamniotic infection is an infection of the amnion or amniotic fluid by any pathogen, and is thought to be a significant cause of idiopathic preterm labor which results in preterm deliveries. Screening for intraamniotic infection involves identifying patients in preterm labor. The standard diagnostic test for intraamniotic infection involves amniocentesis and growing a culture from the extracted amniotic fluid. Because a culture must be grown, diagnosis may take several days and is expensive. Further, diagnosis is often negative in cases where there is significant placental infection or inflammation.

Preeclampsia, an endothelial cell disorder of unknown etiology, occurs in five to seven percent (5–7%) of pregnant women. If undetected and untreated the condition may lead to stillbirth, premature birth, eclampsia or maternal death. The diagnosis of preeclampsia is based on the triad of hypertension, proteinuria and edema. The only known treatment for preeclampsia is delivery of the infant. This is unfortunate because many women with preeclampsia are preterm thereby requiring delivery of a premature infant having the potential for serious neonatal sequelae. Optimally, screening methods to identify those destined to develop preeclampsia would help to study potential treatments aimed at preventing disease manifestations.

The typical screening method for sexually transmitted diseases comprises identifying patients having dysuria and abnormal discharge and the medical practitioner observing whether there is redness, swelling or sores in the genitalia. Additional screening methods include using the leukocyte esterase dipstick or neutrophil quantification on gram chain. Unfortunately these methods have sub-optimal sensitivities and specificities.

Several diagnostic tests for detecting sexually transmitted diseases are readily available in the United States of America and other developed nations. The most accurate diagnostic techniques are polymerase chain reaction and ligase chain reaction which amplify the amount of pathogenic microbial DNA in a patient specimen to detectable levels. Limitations of polymerase chain reaction and ligase chain reaction are the high cost of a medical professional to obtain a specimen from the patient and analyze the results as well as a need for a qualified facility to perform the necessary lab work.

The World Health Organization and some Third World countries use an algorithm comprising a series of questions to screen for sexually transmitted diseases. Because this screening method is based solely on the answers to the questions and not based on a physical assessment of the patient, the degree of error may be high. Further, because of the scarcity of resources in Third World countries, a precise diagnostic test is not performed in cases where the results of the algorithm do not suggest infection thereby missing many patients who truly are infected.

Gonorrhea is caused by the gonococcal bacterium *Neisseria gonorrhea*. If undetected and untreated, gonorrhea can cause postgonococcal nonspecific urethritis, epididymitis, pelvic inflammatory disease, arthritis and possibly death. One method for diagnosing gonorrhea involves taking a scraping from a patient and performing a Gram-stained smear on the scraping. A culture is required for females because the Gram-stain test for gonorrhea is considered less reliable for females. The disadvantage of this detection method is that it is time consuming and costly because it requires a physician to administer the test.

Chlamydia is caused by the bacterium *Chlamydia trachomatous*. If undetected and untreated, chlamydia can cause pelvic inflammatory disease, infertility, ectopic pregnancy and chronic pelvic pain. In addition, undetected chlamydia is thought to cause about fifty percent (50%) of the nonspecific sexually transmitted infections, including nongonococcal urethritis and nonspecific urethritis. A standard method for diagnosing chlamydia involves taking a scraping from a patient which in women, is obtained from the endocervix. The specimen is then placed in a sterile nutritive medium and observed under a microscope for signs of microbial growth and the disease organism. Limitations of this diagnostic method include prolonged incubation, cost and sensitivity of only seventy-five percent (75%) to eighty-five percent (85%).

The scraping may also be subject to antigen detection tests, such as direct fluorescent antibody testing (DFA) and enzyme-linked immunosorbent assay (ELISA) to detect the pathogenic microbial proteins. However, because these methods depend on the presence of antigen, the scraping must include microbial cellular material. Other antigen detection methods for the diagnosis of chlamydia include serological tests involving either complement fixation or microimmunofluorescence. Though antigen detection tests for chlamydia are easily performed and are less costly than cultures however, they have lower sensitivities than cultures and low positive predictive values in low prevalence populations.

Trichomoniasis is caused by the flagellate protozoan *Trichomonas vaginalis*. If undetected and untreated trichomoniasis can cause vaginitis, urethritis, cystitis and prostatitis. The current gold standard for the diagnosis of trichomoniasis is culture on a specimen from the posterior fornix. Although highly sensitive, laboratory availability is limited; therefore, wet mount microscopy conducted on a similar specimen from the posterior fornix is most often used to diagnose this condition. The disadvantage of using this diagnostic test to detect trichomoniasis is that it has a sensitivity of only about fifty percent (50%).

Newer techniques for detecting *Neisseria gonorrhoea*, *Chlamydia trachomatous* and *Trichomonas vaginalis* rely on nucleic acid amplification with subsequent detection. These methods are termed polymerase chain reaction and ligase chain reaction and are considered the most accurate diagnostic methods available. Although commercially available for *Chlamydia trachomatous* they will soon be available for *Neisseria gonorrhoea* and are under development for *Trichomonas vaginalis*. One important aspect of these methods is there reliance only on the presence of a small amount of organism and not in the viability of the organism. This makes it possible for the patient to self-collect a specimen such as urine and/or a swab from the vaginal introitus. Further, as viability is not required a patient can collect the sample and may mail it or delivery it to a reference lab with no decrease in testing sensitivity. The major drawback of these testing methods is the increased cost.

Limitations of the above-noted methods of screening and diagnosing female reproductive tract infections and preeclampsia include inaccuracy, invasiveness, delay between the performance of the test and receipt of the results and need for a medical practitioner to perform the screening or diagnostic tests which results in high cost. Nowhere in the related art is there disclosed or suggested a method and an apparatus for screening for female reproductive tract inflammation and preeclampsia which is inexpensive while being accurate. Therefore, there is a definite need for a method and apparatus for screening for female reproductive tract inflammation and preeclampsia which is inexpensive and effective in order that the general population be tested for these diseases resulting in the diseases being accurately and effectively detected and the patient being treated.

Studies have shown that neutrophil defensins are elevated in blood plasma in patients with either bacterial meningitis or septicemia. This type of method is described in greater detail in *Journal of Laboratory Clinical Medicine*; volume 122 at pp 202–7 (1993). However, the method of detecting female reproductive tract inflammation and preeclampsia disclosed in the present invention which uses the presence of neutrophil defensins found in bodily fluids and tissues such as vaginal fluids or amniotic fluids has never been disclosed or suggested.

SUMMARY OF THE INVENTION

Accordingly, the present invention provides a detection method for reproductive tract inflammation and preeclampsia which combines the accuracy of conventional diagnostic techniques with the convenience and low cost of screening techniques.

The present invention provides a method and apparatus for screening for reproductive tract inflammation and preeclampsia which utilizes the presence of increased levels of neutrophil defensins in bodily fluids or tissue extracted from an animal or human patient to indicate that the patient is at risk of having reproductive tract inflammation or preeclampsia.

Because neutrophil defensins are highly stable and are abundant in human fluids, the method of the present invention is relatively uncomplex. Defensins, also known as human neutrophil peptides (HNP), are cysteine-rich antimicrobial peptides specific to the azurophilic granules of the neutrophil. They constitute greater than five percent (5%) of the total cellular protein and thirty percent (30%) to fifty percent (50%) of the total granule protein. Neutrophil defensins are highly stable to prolonged storage and are resistant to proteolysis and pH effects.

The present invention further provides for the screening of upper reproductive tract inflammation, by measuring neutrophil defensin levels in a specimen extracted from either the endocervical region or vaginal region with the use of a swab or dipstick. This method is more precise than a pelvic exam alone and less expensive and time consuming than a Gram-stain or a culture. When screening specifically for pelvic inflammatory diseases, the present invention allows patients who do not have a pelvic inflammatory disease to avoid the invasive and expensive diagnostic procedure of endometrial biopsy.

The present invention may also be used to detect intraamniotic infections. Amniotic fluid is withdrawn by amniocentesis, and defensin levels within the extracted amniotic fluid are detected. This is faster than the conventional method of culturing amniotic fluid.

The present invention also provides for screening for preeclampsia by detecting neutrophil defensins in plasma. The present invention provides for the detection of preeclampsia in "low-risk" patients prior to the development of clinical symptoms. This may allow for the development of effective treatments to prevent the condition or earlier interventions to prevent the maternal/fetal morbidity associated with clinical presentation.

When screening for gonorrhea, chlamydia or trichomoniasis, the present invention tests vaginal and cervical fluid samples for elevated antimicrobial peptide levels. It is preferred that the sample be taken from the vaginal introitus. By taking the sample from the vaginal introitus rather than the conventional site of the endocervix, the sample can be taken without the use of a speculum and without the aid of medical professionals. This results in the screening method being inexpensive and being accurate.

The present invention further provides an apparatus which allows the patient to take the sample, run the test and use the results to decide if further diagnostic testing is necessary. Because self-testing avoids involvement by medical professionals it is inexpensive and convenient. Self-testing also saves time because it does not require the use of a laboratory with its time-consuming shipping and record-keeping requirements. In addition, the present invention give results within a few minutes, whereas a laboratory test may take several weeks.

Furthermore, because self-testing provides privacy, low cost and convenience, it would be likely that more women would be screened at an earlier stage of a sexually transmitted disease resulting in more patients at high risk seeking immediate diagnosis and necessary treatment. This would lead to earlier detection and treatment of a greater number of sexually transmitted disease carriers and lower incidence of sexually transmitted diseases in the general population.

Other details, objects and advantages of the present preferred invention will become more apparent with the following description of the present preferred invention.

BRIEF DESCRIPTION OF THE DRAWINGS

The accompanying drawings and graphs describe the present preferred invention in which:

FIG. 1c is a cross-sectional view of the dipstick shown in FIG. 1b immersed in the solution containing the specimen shown in FIG. 1a.

DETAILED DESCRIPTION OF THE PRESENT PREFERRED INVENTION

Although this invention is suitable for other uses, such as detecting reproductive tract infections in male humans and other animals, it will be described as being used to detect reproductive tract inflammation and preeclampsia in females. Such description is for purposes of explanation and is not intended to limit the scope of this invention.

In the preferred embodiment of the present invention, the antimicrobial peptides whose levels are measured are the defensins known as human neutrophil peptides 1, 2 and 3 (HNP1–3). Defensins are neutrophil granule products that are highly stable to prolonged storage and resistant to proteolysis and pH effects. In the presence of infection, neutrophils are the initial cell recruited to the site of inflammation. Once present they attack and ingest the invading microbes leading to a release of granule products such as defensins. Because defensins are abundant in patients with infections, intraamniotic infection and preeclampsia and because they are stable, defensins are easier to detect than other neutrophil products. In addition, defensins such as HNP1–3 are specific to neutrophil and therefore are more specific to inflammatory diseases than many other peptides, such as leukocyte esterase.

The preferred method of measuring HNP1–3 in a sample of bodily fluid or tissue is by an antigen detection method termed enzyme-linked immunosorbent assay (ELISA). Enzymelinked immunosorbent assay is preferred because of its enhanced sensitivity to small amounts of peptides. The monoclonal antibodies needed for the enzyme-linked immunosorbent assay can be prepared using hybridoma preparation techniques that can be derived from known secreting hybridomal cell lines such as those available from Panyutich et al. which are specific to defensins. This technique is a mini-plate based assay which utilizes monoclonal antibody D-1-1 to capture defensins followed by detection with a monoclonal antibody D1–11 which is labelled with biotin. The monoclonal antibody D-1-1 and D1–11 are further described in Panyutich et al., *An Enzyme Immunoassay For Human Defensins*, J. Immunol. Meth. 1991; 141:149–155. The monoclonal antibody D-1-1 is deposited with the American Type Tissue Collection in Bethesda and identified by accession number HB 11462. Enzyme-linked immunosorbent assay is further described in *European Journal of Immunology*, Kohler et al., Volume 6 at p 292, (1976).

Figure 1A:
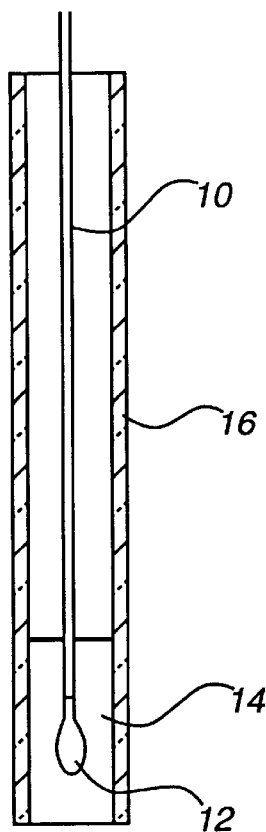
FIG. 1a is a cross-sectional view of a swab containing a specimen being immersed into a solution in accordance with the present invention.
Figure 1B:
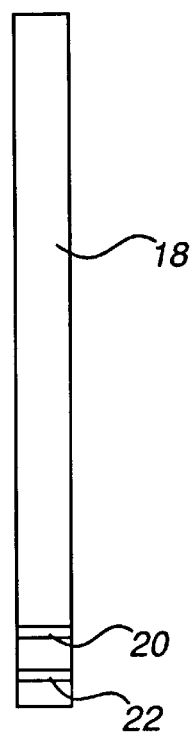
FIG. 1b is an elevational view of the dipstick of the present invention.
Figure 1C:
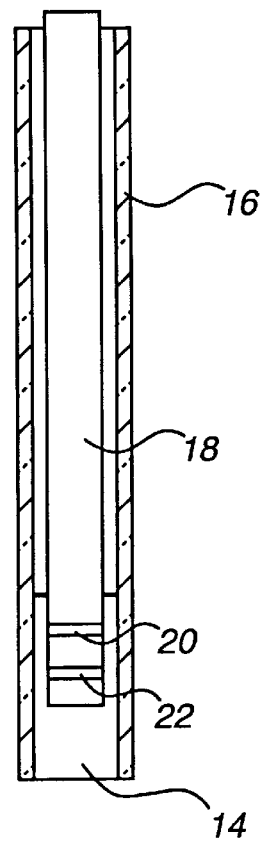
Figure 2A:
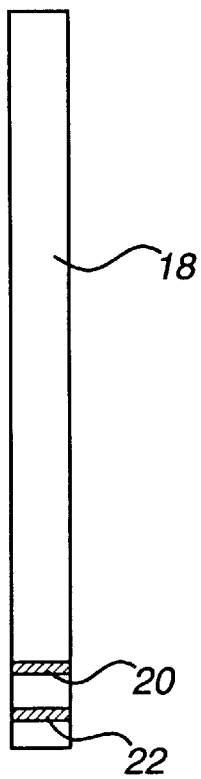
FIG. 2a is an elevational view of the dipstick shown in FIG. 1b wherein the dipstick indicates a positive test.
Figure 2B:
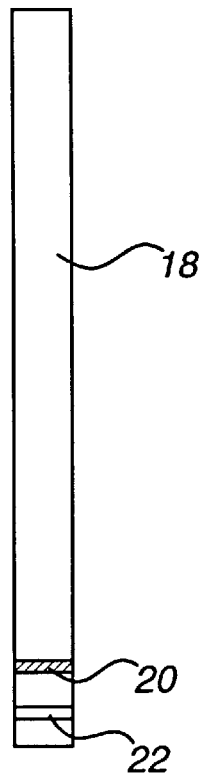
FIG. 2b is an elevational view of the dipstick shown in FIG. 1b wherein the dipstick indicates a negative test.

In a preferred embodiment of the present invention, screening for sexually transmitted diseases such as gonorrhea, chlamydia and trichomoniasis may be accomplished by the patient using a home test kit in the form of a dipstick-based assay as shown in FIGS. 1 and 2. The dipstick-based assay home test kit measures the levels of any one or combination of HNP1–3 in samples taken from the vagina. The home test kit is provided with a swab 10 having a tip 12 in order that a specimen can be taken from the vaginal area of the patient. The home kit further has a phosphate buffered salient solution 14 contained within a receptacle 14 and a dipstick 18 having a control site 20 and a test site 22, both indicated by hidden lines. The control site is labeled non-specifically with your detection apparatus and should change color when the dipstick is utilized. However, if a specimen or solution 14 is faulty, the control site will not change color. The test site 22 is treated with an amount of monoclonal antibody D1-1 such that if the specimen contains a level of HNP1–3 below the cut-off point it will not change color. However if it contains a level of defensins above the cut-off point it will change color.

Figure 2C:
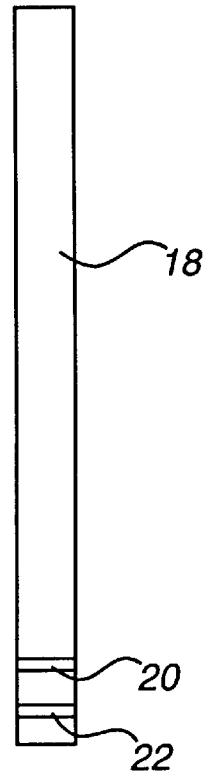
FIG. 2c is an elevational view of the dipstick shown in FIG. 1b wherein the dipstick indicates a faulty test.

After the specimen is captured on the swab tip 12, the swab 10 is immersed in the phosphate buffered solution 14 such that the solution 14 contains the specimen. The dipstick 18 is then immersed in the phosphate buffered solution 14 containing the specimen. The dipstick 18 is extracted from the solution 14 and one of the three scenarios shown in FIG. 2 will result. Both the test site 22 and the control site 20 may change color as shown in FIG. 2a which would indicate that the patient tested positive meaning that the patient is at risk of having the sexually transmitted disease. Alternatively, a negative reading may be obtained when the control site 20 changes color and the test site 22 does not change color. A negative reading indicates that the patient is not at risk of having the sexually transmitted disease and there is no need to undergo expensive diagnostic tests. The last possible scenario is shown in FIG. 2c wherein neither the control site 20 nor the test site 22 changes color indicating that a faulty test. In this instance, the patient or doctor should administer the test again. It is preferred that the means for extracting the specimen be able to store the specimen such that the specimen is able to be transferred to a laboratory for further diagnostic testing. The home test kit may take a similar form to that of any of the conventional home pregnancy tests. The likely antibody congugales will be colloidal gold or latex beads.

The preferred method of the invention comprises extracting a sample of bodily fluid or tissue from a patient, measuring the amount of antimicrobial peptides in the sample preferably by enzyme-linked immunosorbent assay or dipstick assay, comparing the amount of HNP1–3 with a known normal level and indicating to the patient if the sample contains an amount of HNP1–3 that exceeds the known normal level which signifies that the patient is at risk of having a sexually transmitted disease.

Although other sites can be used to extract a sample of bodily fluid or tissue from the patient such as the cervix or the mouth, the vagina is the preferred test site for several reasons. First, it is a less invasive site than other test sites, such as the cervix. Second, a vaginal test site allows for self-testing with the home test kit. Finally, the vagina is a preferred test site because there is a pronounced difference in the level of HNP1–3 for each type of sexually transmitted disease measured.

Figure 3:
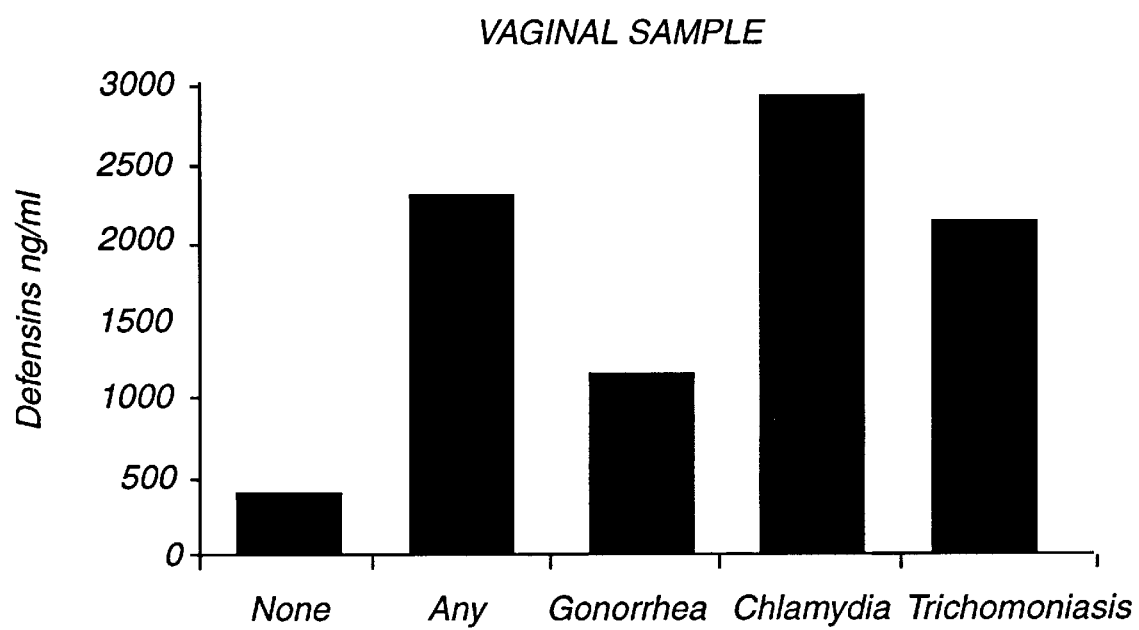
FIG. 3 illustrates the defensin levels measured in vaginal fluids of women.
Figure 4:
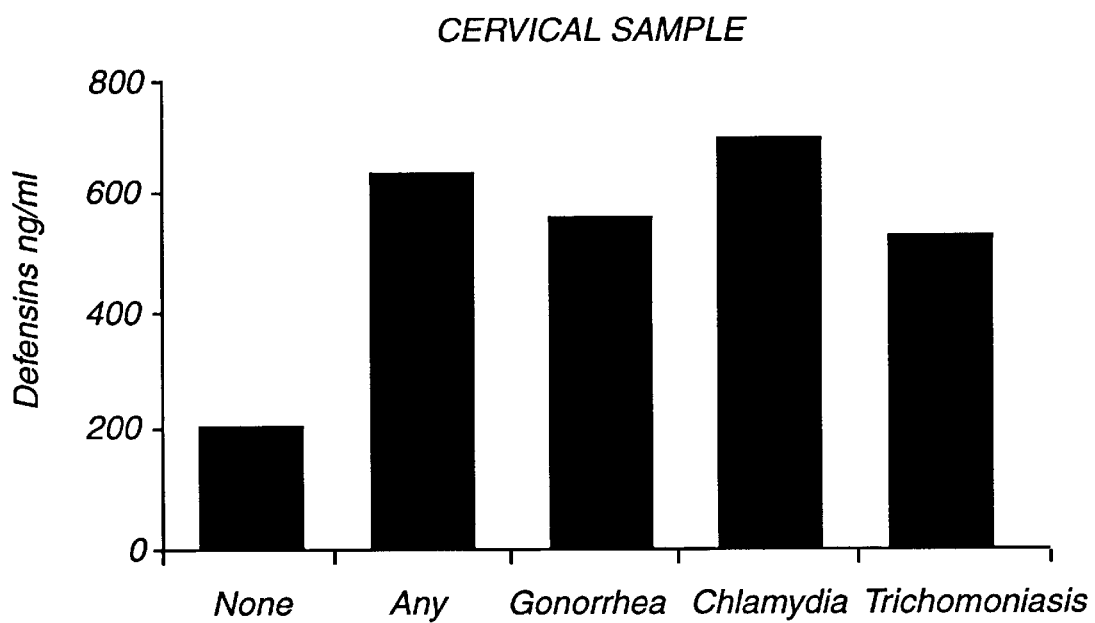
FIG. 4 illustrates the defensin levels measured in cervical samples of women.

Defensin levels were measured in vaginal and cervical fluids of 300 women presenting for sexually transmitted disease evaluation at a county health department and the results are presented in FIG. 3 and FIG. 4, respectively. Referring to FIG. 3, in women who had no infection (n=199), median vaginal HNP1–3 levels were 400 ng/ml with a 95% confidence interval (CI) of 201.2–562.2. In women with gonorrhea (n=34), HNP levels were 1200 ng/ml, with a 95% CI of 690–3360. In women with chlamydia (n=37), median HNP levels were 2900 ng/ml, with a 95% CI of 816–3950. In a woman with trichomoniasis (n=61), median HNP levels were 2200 ng/ml, with a 95% CI of 710–4055.

Referring to FIG. 4, in women who had no infection (n=199), median cervical HNP1–3 levels were 200 ng/ml, with a 95% CI of 130–300. In women with gonorrhea (n=34), median cervical HNP1–3 levels were 560 ng/ml, with a 95% CI of 220–990. In women with chlamydia (n=37), median cervical HNP levels were 650 ng/ml, with a 95% CI of 290–950. In women with trichomoniasis (n=61), median cervical HNP levels were of 550 ng/ml, with a 95% CI of 360–850.

Because of the clear differences in HNP levels for each of gonorrhea, chlamydia and trichomoniasis, measurement of HNP1–3 in vaginal samples may not only be used as a screen for sexually transmitted diseases in general, but as an indicator of which sexually transmitted disease a woman might have. If the present invention screening method indicates that the patient is at risk of having a sexually transmitted disease, the stability of defensins would allow the patient, without visiting a health provider, to send the sample of vaginal fluid to a lab for a precise diagnosis. This indication would help steer the laboratory or health provider to the correct diagnostic test for confirmation of a particular sexually transmitted disease, and lead to lower costs, faster diagnosis and, ultimately, faster treatment.

Figure 5:
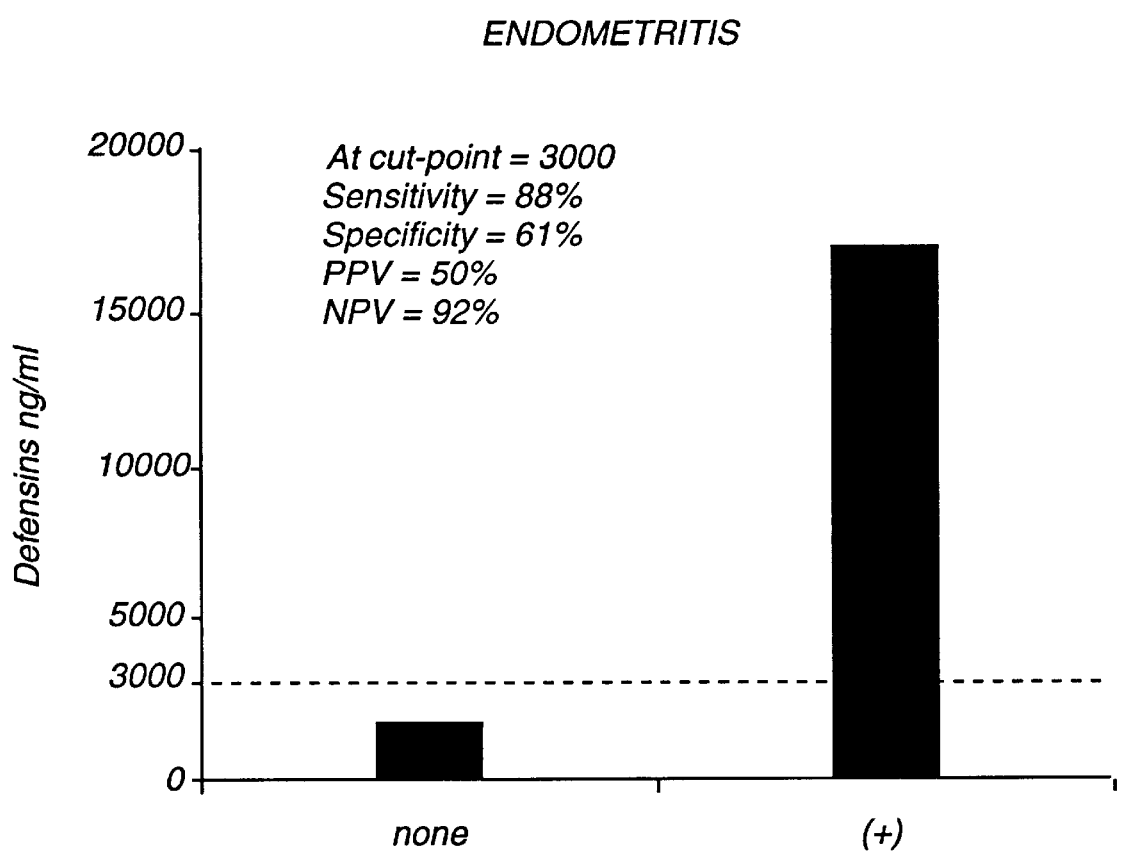
FIG. 5 illustrates the defensin levels measured in endocervical samples of women.

In the preferred embodiment of the present invention, screening for upper reproductive tract inflammation such as endometritis is accomplished by measuring levels of HNP1–3 in a sample taken from the endocervix. This would replace the need for the highly invasive endometrial biopsy or diagnostic laparoscopy. Defensin levels were measured in endocervical samples of twenty-three (23) women presenting for sexually transmitted disease evaluation and the results are depicted in FIG. 5. Patients who had no infection or inflammation (n=16) had median HNP1–3 levels of 1687 ng/ml, with a standard error of 1201. Patients who had endometritis (n=7) had median HNP1–3 levels of 17,017 ng/ml with a standard error of 4458. Descriptive statistics for how test using a cut-point of 3000 ng/ml are also presented.

Figure 6:
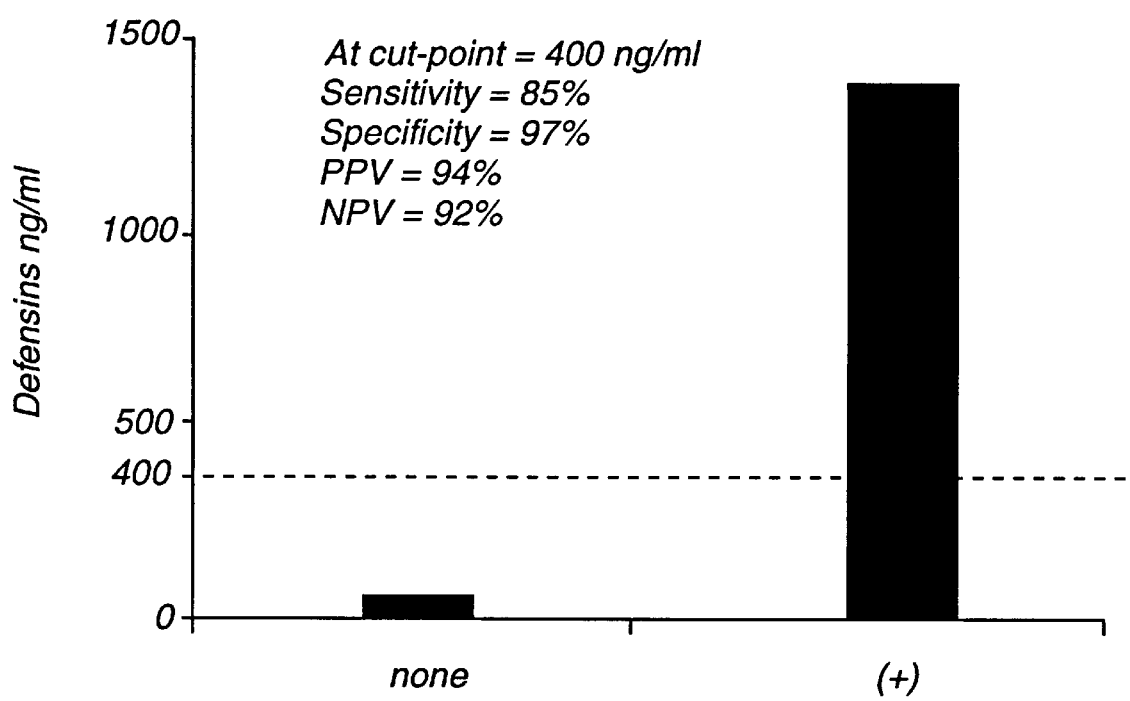
FIG. 6 illustrates defensin levels measured in amniotic fluids of women.

In the preferred embodiment of the present invention, diagnosis of intraamniotic infection is accomplished by measuring levels of HNP1–3 in a sample of amniotic fluid. Amniotic fluid HNP1–3 levels of 53 patients presenting in preterm labor were measured and the results thereof are depicted in FIG. 6. In those defined as having intraamniotic infection by either a positive culture or significant placental history, median HNP1–3 levels were 1,351.50 ng/ml with a standard error of 29,379 ng/ml. Patients who were not infected had median HNP1–3 levels of 49 ng/ml with a standard error of 16.89 ng/ml. Descriptive statistics utilizing a cut point of 400 ng/ml are also presented.

Figure 7:
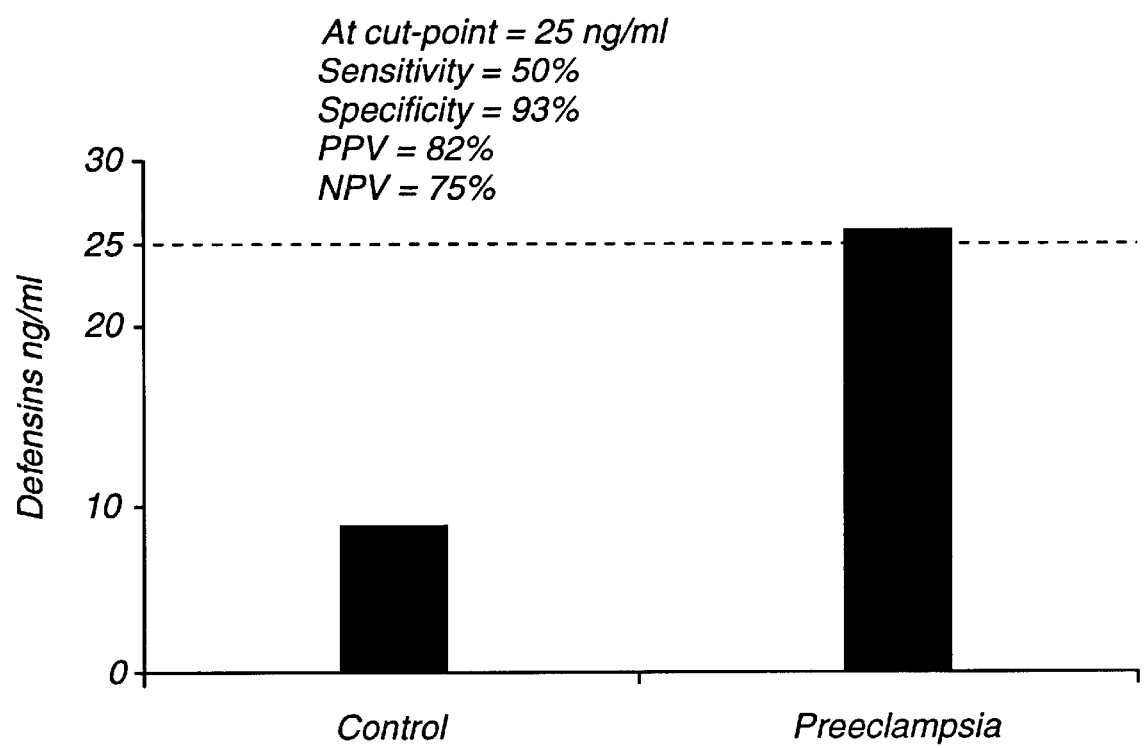
FIG. 7 illustrates defensin levels measured in plasma of both preeclamptic and control women.

In the preferred embodiment of the present invention, screening for preeclampsia is accomplished by measuring levels of HNP1–3 in plasma. Defensin levels in preeclamptic patients were compared with those in control patients who delivered at term without preeclampsia and the results are depicted in FIG. 7. Control patients without preeclampsia had median HNP1–3 levels of 9 ng/ml, with a standard error of 8.6. Patients who had preeclampsia had median HNP1–3 levels of 26 ng/ml with a standard error of 16.2. Descriptive statistics using a cut point of 25 ng/ml are also presented.

Although sensitivity of the present invention method for screening of preeclampsia is only fifty percent (50%), the specificity is a much higher ninety-three percent (93%). Therefore, HNP1–3 sensing would identify 50% of women diagnosed for preeclampsia without many false positive and would prove extremely beneficial in studying potential treatments for this condition.

Although not described in detail, the present invention provides for the above procedures may be used to detect HNP4 levels or other members of the defensin family, either alone or in combination with HNP1–3. Further the present invention can also be utilized to measure HNP levels in various other samples not described above such as mucosal samples taken from men or other animals to screen for reproductive tract disease.

While the present invention has been described herein, it is distinctly understood that the invention is not limited thereto but may be otherwise variously embodied the scope of the following claims and any equivalent thereof.

I claim:

1. A method of screening for one or more disorders in a human patient, said one or more disorders selected from the group consisting of reproductive tract disease, reproductive tract inflammation and preeclampsia, said method comprising the steps of:

(a) extracting a sample comprising a bodily fluid or a tissue from the patient;

(b) measuring the amount of Human Neutrophil Peptide 1–3 defensins present in said sample;

(c) comparing said measured amount of defensins HNP1–3 with a known normal level of defensins HNP1–3 expected for a normal said sample: and, (d) if said measured amount of defensins HNP1–3 exceeds said known normal level of defensins HNP1–3 by at least a predetermined amount then correlating the measured amount of defensins HNP1–3 with known abnormal defensin HNP1–3 levels indicative of said one or more disorders, thereby providing a positive screen for said one or more disorders.

2. The method of claim 1, wherein the patient is a female.

3. The method of claim 2, wherein the one or more disorders is the reproductive tract infection endometritis and the sample is endocervical fluid.

4. The method of claim 2, wherein the one or more disorders is preeclampsia and said sample is plasma.

5. The method of claim 2, wherein said one or more disorders is an amniotic infection and said sample is amniotic fluid.

6. The method of claim 1, wherein the one or more disorders is a reproductive tract disease selected from the group consisting of gonorrhea, trichomoniasis and chlamydia.

7. The method of claim 6, wherein said sample is vaginal fluid, cervical fluid and amniotic fluid.

8. The method of claim 7, wherein said sample is vaginal fluid.

9. The method of claim 1, wherein the step of measuring is performed by an enzyme-linked immunosorbent assay.

10. A method of screening for one or more disorders in a human patient, said one or more disorders selected from the group consisting of reproductive tract disease, reproductive tract inflammation and preeclampsia, said method comprising the steps of:

(a) measuring the amount of defensins HNP1–3 present in a sample previously taken from said patent;

(b) comparing said measured amount of defensins HNP1–3 with a predetermined maximum normal level of defensins HNP1–3; and, (c) if said measured amount of defensins HNP1–3 exceeds said predetermined maximum normal level of defensins HNP1–3 by at least a predetermined amount, then correlating the measured amount of defensins HNP1–3 with known abnormal defensin HNP1–3 levels indicative of said one or more disorders, thereby providing a positive screen for said one or more disorders.

* * * * *